US008084032B2

(12) United States Patent
Yumioka et al.

(10) Patent No.: US 8,084,032 B2
(45) Date of Patent: Dec. 27, 2011

(54) PURIFICATION METHOD WHICH PREVENTS DENATURATION OF AN ANTIBODY

(75) Inventors: Ryosuke Yumioka, Kanagawa (JP);
Daisuke Ejima, Kanagawa (JP);
Tsutomu Arakawa, Thousand Oaks, CA (US)

(73) Assignee: Ajinomoto Co., Inc., Tokyo (JP)

( * ) Notice: Subject to any disclaimer, the term of this patent is extended or adjusted under 35 U.S.C. 154(b) by 1293 days.

(21) Appl. No.: 11/030,088

(22) Filed: Jan. 7, 2005

(65) Prior Publication Data

US 2005/0176109 A1 Aug. 11, 2005

Related U.S. Application Data

(60) Provisional application No. 60/537,503, filed on Jan. 21, 2004, provisional application No. 60/631,407, filed on Nov. 30, 2004.

(51) Int. Cl.
*A61K 39/395* (2006.01)
(52) U.S. Cl. .................................. 424/176.1; 424/177.1
(58) Field of Classification Search ........................ None
See application file for complete search history.

(56) References Cited

U.S. PATENT DOCUMENTS 6,171,586 B1 * 1/2001 Lam et al. .................. 424/130.1

FOREIGN PATENT DOCUMENTS

| EP | 0 310 719 | 4/1989 |
| JP | 2-273194 | 11/1990 |
| WO | WO 94/07912 | 4/1994 |
| WO | WO 02/098531 | 12/2002 |

OTHER PUBLICATIONS

Protein Purification Handbook (1999, p. 1-27,29-59,61-97, Amersham Pharmacia Biotech).*
Tsumoto et al. (Biotechnol. Prog. 2004, 20:1301-1308).*
Arakawa et al., Biochem. Biophysical Research Communications 304, 2003, p. 148-152.*
Uemura, Tohoku J. Exp. Med, 1983, vol. 141, 337-349.*
Arakawa, T., et al., "Elution of antibodies from a Protein-A column by aqueous arginine solutions," Protein Expression and Purification 2004;36:244-248.
Bywater, R., et al., "Elution of Immunoglobulins from Protein A—Sepharose® CL4B Columns," 1976 Meeting Proceedings, vol. 2, pp. 337-340.
"Strategies for antibody purification," Life Science News, Amersham Biosciences 2002;12:1-2.
Kent, U. M., Methods in Molecular Biology, col. 115, 1999, pp. 29-33, XP008043501 Totowa, NJ, US.
Notification of Reason for Rejection for Japanese Patent App. No. 2005-013897 (Sep. 16, 2010) with English translation thereof.
Arora, D., et al., "Method for increasing the yield of properly folded recombinant human gamma interferon from inclusion bodies," (1996) J. Biotechnol. 52, 127-133.
Boschetti, E., "Antibody separation by hydrophobic charge induction chromatography,"(2002) Trends Biotechnol. 20, 333-337.
Brinkmann, U., et al., "Independent domain folding of *Pseudomonas* exotoxin and single-chain immunotoxins: influence of interdomain connections," (1992) Proc. Natl. Acad. Sci. USA. 89, 3075-3079.
Brown, N. L., et al., "A study of the interactions between an IgG-binding domain based on the B domain of staphylococcal protein a and rabbit IgG," (1998) Mol. Biotech. 10, 9-16.
Buchner, J., et al., "Alternatively folded states of an immunoglobulin," (1991) Biochemistry 30, 6922-6929.
Buchner, J., "Renaturation, purification and characterization of recombinant Fab-fragments produced in *Escherichia coli*," (1991) Bio/Technology 9, 157-162.
Calmettes, P., et al., "Temperature and pH dependence of immunoglobulin G conformation," (1991) Arch. Biochem. Biophys. 291, 277-283.
Fahrner, R. L., et al., "Performance comparison of protein A affinity-chromatography sorbents for purifying recombinant monoclonal antibodies," (1999) Biotech. Appl. Biochem., 30, 121-128.
Gülich, S., et al., "Protein engineering of an IgG-binding domain allows milder elution conditions during affinity chromatography," (2000) J. Biotechnol. 76, 233-244.
Gupta, R. C., et al., "Isolation of circulating immune complexes by conglutinin and separation of antigen from dissociated complexes by immobilized protein A," (1981) Clin. Exp. Immunol. 46, 9-19.
Hanh, R., et al., "Comparison of protein A affinity sorbents," (2003) J. Chromatogr. B., 790, 35-51.
Jiskoot, W., et al.., "Non-random conformation of a mouse $IgG_{2a}$ monoclonal antibody at low pH," (1991) Eur. J. Biochem., 201, 223-232.
Jiskoot, W., et al., "Analytical approaches to the study of monoclonal antibody stability," (1990) Pharm. Res. 7, 1234-1241.
Li, R., et al., "Design, synthesis, and application of a protein A mimetic," (1998) Nat. Biotechnol. 16, 190-195.
Martsev, S. P., et al., "Large increase in thermal stability of CH2 domain of rabbit IgG after acid treatment as evidenced by differential scanning calorimetry, " (1994) Immunol. Lett. 43, 149-152.
Martsev, S. P., et al., "Thermodynamic and functional characterization of a stable IgG conformer obtained by renaturation from a partially structured low pH-induced state," (1995) FEBS Lett. 361, 173-175.
Narhi, L., et al., "Effect of three elution buffers on the recovery and structure of monoclonal antibodies," Anal. Biochem. 253 (1997), 236-245.
Paborji, M., et al., "Chemical and physical stability of chimeric L6, a mouse-human monoclonal antibody," (1994) Pharm. Res. 11, 764-771.
Sarciaux, J. M., et al., "Effects of buffer composition and processing conditions on aggregation of bovine IgG during freeze-drying," (1999) J. Pharm. Sci. 88, 1354-1361.
Shiraki, K., et al., "Biophysical effect of amino acids on the prevention of protein aggregation," (2002) J. Biochem. 132,591-595.

(Continued)

*Primary Examiner* — Yunsoo Kim
(74) *Attorney, Agent, or Firm* — Shelly Guest Cermak; Cermak Nakajima LLP (57) ABSTRACT

The present invention provides a method of purifying an antibody by protein A affinity chromatography. More specifically, the present invention provides a technique relating to an elution buffer solution which provides a good antibody recovery rate without denaturation.

14 Claims, 6 Drawing Sheets

OTHER PUBLICATIONS

Thies, M. J. W., et al., "The alternatively folded state of the antibody $C_H3$ domain," (2001) J. Mol. Biol. 309, 1077-1085.

Tsumoto, K., et al., "Practical considerations in refolding proteins from inclusion bodies," (2003) Protein Expr. Purif. 28, 1-8.

Tsumoto, K., et al., "Solubilization of active green fluorescent protein from insoluble particles by guanidine and arginine," (2003) Biochem. Biophys. Res. Commun. 312, 1383-1386.

Varady, L., et al., "Rapid high-performance affinity chromatography on micropellicular sorbents," (1988) J. Chromatogr. 458, 207-215.

Verdoliva, A., et al., "Affinity purification of polyclonal antibodies using a new all-D synthetic peptide ligand: comparison with protein A and protein G," (2002) J. Immunol. Methods 271, 77-88.

Vermeer, A. W. P., et al., "The thermal stability of Immunoglobulin: Unfolding and aggregation of a multi-domain protein," (2000) Biophys. J. 78, 394-404.

Vlasov, A. P., et al., "Non-native conformational states of immunoglobulins: Thermodynamic and functional studies of rabbit IgG," (1996) Biochemistry (Moscow) 61, 155-171.

Welfle, K., et al., "Conformation, pH-induced conformational changes, and thermal unfolding of anti-p24 (HIV-1) monoclonal antibody CB4-1 and its Fab and Fc fragments," (1999) Biochim Biophys. Acta 1431, 120-131.

* cited by examiner

[Fig. 1] Gel permeation HPLC of recovered antibody of Table 1 (Experimental Conditions 1 to 4)

[Fig. 2] Protein A chromatogram of antibody using arginine elution buffer solutions of Table 2

[Fig. 3] Gel permeation HPLC of recovered antibody of Table 2 (Experiment Nos. 1 and 2)

[Fig. 4] Gel permeation HPLC of recovered antibody of Table 3 (Experiment Nos. 1 and 2)

[Fig. 5] Gel permeation HPLC of recovered antibody of Table 4 (Experiment Nos. 1, 2 and 3)

[Fig. 6] Reference Example: Gel permeation HPLC of antibody recovered using 0.1 M sodium citrate at pH 2.9

PURIFICATION METHOD WHICH PREVENTS DENATURATION OF AN ANTIBODY

This application claims priority under 35 U.S.C. §119(e) to provisional application 60/537,503, filed on Jan. 21, 2004 and 60/631,407, filed on Nov. 30, 2004

BACKGROUND OF THE INVENTION

1. Field of the Invention

The present invention relates to a method of purifying an antibody employing protein A affinity chromatography. More specifically, the present invention relates to an elution buffer component useful in the method.

2. Brief Description of the Related Art

Antibodies are extremely useful in drug formulations, as clinical examination reagents, and as research reagents. Hence, demand for them is increasing. Staphylococcal Protein A ("protein A" hereinafter), an Fc receptor derived from a microbe, exhibits extremely high affinity for multiple antibody Fc domains. Thus, affinity chromatography employing immobilized protein A as a ligand on a support has become the core technique in industrial-scale antibody manufacturing (for example, see The Production of Monoclonal Antibodies. In Birch, J. R. and Lennox, E. S. (ed.); Monoclonal Antibodies, Principles and Applications, p. 231-265, London: Wiley Liss, Inc., 1995). The high affinity of protein A increases production efficiency per unit time, and contributes to the elimination of impurities which originate in the starting materials to a high degree. However, problems due to antibody characteristics remain in Protein A affinity chromatography, limiting antibody production. The present invention solves these problems relating to antibody characteristics and affords improvement toward more stable manufacturing of antibody.

Protein A exhibits extremely high affinity for Fc domains at neutral pH. Thus, starting material containing antibody to be purified can be loaded onto a column packed with support upon which protein A has been immobilized at neutral pH. After thorough washing with neutral pH buffer solution to remove impurities in the starting materials, the antibody can be desorbed from the column with an elution buffer solution of acidic pH, specifically, from pH 2.5 to less than pH 4. Impurities deriving from the starting materials that remain in the antibody after desorbtion at acidic pH are present on the order of only several hundred ppm, and the various immobilized protein A supports that can be used for industrial production are known to present no difference in basic performance (for example, see R. L. Fahrmer, D. H. Whitney, M. Vandertaan, G. Blank, Biotech. Appl. Biochem (1999) 30, 121-128 and R. Hahn, R. Schlegel, A. Jungbauer, J. Chromatogr. B., (2003) 790, 35-51). Currently, immobilized protein A supports suitable for use in industrial antibody production are commercially available from Amersham Biosciences, Inc., Millipore, PE Biosystems Corp., and the like. However, common problems are encountered when purifying antibody with these supports. The antibody that is desorbed from the support and recovered comes in contact with a highly acidic buffer solution, altering the tertiary structure of the antibody.

Furthermore, association and aggregation tend to occur during frequently. Extensive research into changes in antibody structure caused by acidic pH has been conducted. However, resolution of the issues regarding structural change and the association and aggregation reactions has yet to be proposed. The fact that exposure to acidic pH causes certain problems in antibodies has been reported chiefly as a practical problem. See J. M. Sarciax et al., *Journal of Pharmaceutical Sciences,* 88 (1999), 1354-1361; and M. Paborji et al., *Pharmaceutical Research,* 11(1994), 764-771. The fact that acidic pH causes changes in the tertiary structure of an antibody has been demonstrated in a number of experiments. See Buchner et al., *Biochemistry,* 30 (1991), 6922-6929; Buchner et al., *Biophysical Journal* 78 (2000), 394-404; and Buchner et al., *Biochimica et Biophysica Acta,* 1431 (1999), 120-131. Vlasov et al. reports the effect that even when an antibody is titrated to neutral pH without having undergone association or aggregation as a result of contact with acidic pH, the original antibody structure cannot be restored. See Vlasov et al., *Biochemistry (Moscow),* 61 (1996), 155-171; Vlasov et al., *Immunology Letters,* 43 (1994), 0.149-152; Vlasov et al; *FEBS Letters,* 361 (1995), 173-175. Since the goal of purification is to retain the quality of antibody, acidic pH exposure is extremely undesirable. Therefore, there exists the need for a new refinement technique that does not require exposure to acidic pH.

Extensive research has been conducted into solving the above-stated problem. A number of examples of such research will be summarized and the problems of prior art will be enumerated below.

(1) Methods of Recovering Antibody from Protein A in Neutral Buffer Solution

Based on the knowledge that tyrosine residues participate in the binding of protein A and antibody Fc domains, it was discovered that a dipeptide containing tyrosine (0.1 M glycyltyrosine, pH 7.0) could be used instead of an acidic elution buffer solution to desorb and recover antibody from protein A-binding support. See Bywater et al., Chromatogr. Synth. Biol. Polym., [Lect. Chem. Soc. Int. Symp.] 1978; Bywater et al., 1976 Meeting Proceedings, Volume 2, 337-340. However, there is a limit in that only about 20 to 35 percent of the bound antibody can be recovered under these conditions, rendering this method impractical.

Based on the knowledge that histidine residues participate in the binding of protein A and antibody Fc domains, it was discovered that not histidine alone but an imidazole solution (1 to 5 M, pH 6 to 9) corresponding to histidine residues could be employed instead of an acidic elution buffer solution to desorb and recover antibody from the protein A-binding support. See WO94/07912. However, this technique requires 1 to 5 M (3 M or better for good recovery) high-concentration imidazole elution. An imidazole solution is used as an elution buffer solution in metal chelate affinity chromatography for refinement of other substances such as fused proteins with a bound histidine tag are employed. However, it is well known by researchers in this field that imidazoles themselves denature proteins, and are unsuitable as elution buffer solutions for antibody purification. Thus, this method has also been found impractical.

(2) Methods of Employing Artificial Ligands in Which the Amino Acid Sequence of Protein A has been Altered S. Hober et al. focused on domain B as the domain at which protein A binds to antibody Fc, creating an artificial Z domain by changing a portion of the amino acid sequence of domain B. It has been shown that supports having immobilized domain Z as ligand binds well to antibody at neutral pH and permits efficient recovery of bound antibody using a mildly acidic buffer solution of pH 4.5 instead of an acidic elution buffer solution. See Hober et al., *J. Chromatogr.* 76 (2000) 233-244. However, the affinity of domain Z for antibody at neutral pH is much lower than that of protein A, and the decrease in production efficiency which accompanys the decrease in antibody binding capacity is a major problem.

Further, the decrease in affinity relates to a decrease in the capability to eliminate impurities from the starting materials, so the problem of maintaining the quality of the product remains. Thus, this method has also been found to be impractical.

Based on X-ray crystal structure analysis of the protein A—antibody Fc domains complex, a number of variant forms of protein A were created in which the hydrophobic residues on the protein A molecule that participate in binding of the two molecules were replaced with histidine. Of these, whereby the Protein A leucine at residue numbers 21 and 79 was replaced with histidine, it was discovered that a decrease of pH 8 to only pH 5 in the buffer solution reduced affinity to antibody Fc domains to $1/50^{th}$ the previous level. When the mildly acidic pH 5.0 buffer solution was employed instead of the acidic elution buffer solution, the antibody bound to the variant protein A could be effectively recovered. See M. G. Gore et al., *Molecular Biotechnology* 10 (1998), 9-16. However, the affinity of the variant protein A for antibody Fc domains at pH 8 is only $1/5^{th}$ that of protein A. Similar to the above Z domain, there are significant problems such as decreased production efficiency and a decreased capability to eliminate impurities. Thus, this method has also been found impractical.

(3) Methods Employing Ligands Synthesized by Organic Chemistry Instead of Protein A A compound was designed which undergoes a change in a hydrophobic property with a change in pH, irrespective of protein A. It was further discovered that this compound exhibits affinity for antibody Fc domains in a pH-dependent manner, and an antibody purification support was developed upon which this compound was bound as ligand. See Boschettir, *Trends Biotechnol.* 20 (2002), 333-337. This support can be purchased from Biosepra Corp. as MEP Hypercel. This support permits the recovery of bound antibody using a mildly acidic buffer solution (pH 4 to 5). However, the pH-dependent change in affinity is not as sharp as that of protein A, and desorption and recovery from the support when in concentrated form are impossible. Binding specificity is also much poorer than that of protein A, preventing the removal of impurities derived from the starting materials to a high degree. Although it is possible to set special washing conditions (using an organic acid or the like) suited to starting material purification to enhance the purification effect, the effect is still quite inferior to that of purification by protein A. Thus, this compound has not replaced protein A in industrial production.

A peptide mimicking the binding portion of protein A on antibody Fc domains was devised, and this structure was further developed, creating protein A-mimicking ligands completely synthesized by organic chemistry. See L. R. Down et al.; Mabsorbent®: *Nature Biotechnology* 16 (1998), 190-195. Antibody bound by these synthetic ligands can normally be desorbed and recovered at pH 3.0 with 10 mM sodium citrate, with the use of a neutral pH buffer solution being possible in the presence of ethylene glycol. However, since binding specificity is significantly poorer than that of protein A, the capability to eliminate impurities derived from starting materials is quite inferior to that of protein A. In a manner similar to that of the above MEP Hypercel, and since these synthetic ligands were primarily developed for use without protein A, a protein ligand, a decrease in the capability to eliminate impurities is considered inevitable. These synthetic ligands have not replaced protein A in industrial production, and are an inadequate solution to the problems of acidic elution buffer solutions.

(4) Methods Employing Protein A with an Acidic Elution Buffer Solution While Stabilizing the Antibody As set forth above, it has not proved easy to develop an antibody purification method that can effectively replace protein A and acidic elution buffer solutions. Accordingly, methods of preventing the denaturation (structural change, association and aggregation reactions) of an antibody following contact with acidic elution buffer solution have been proposed.

Following the recovery of antibody bound to protein A with an acidic elution buffer solution, a stabilizing agent was immediately added in the form of a polyol compound such as polyethylene glycol, polyvinyl pyrrolidone, or ethylene glycol, to suppress association and aggregation reactions. See Japanese Patent Application No. Hei 2-273194. Based on this method, the addition of a stabilizing agent as soon as possible following contact with an acidic buffer solution suppresses the association and aggregation reactions, but the structural change at an acidic pH as set forth above cannot be suppressed. Furthermore, instead of using a stabilizer in the form of the polyol as proposed by Higuchi et al., a change in the pH itself must be prevented. See Carpenter et al., *Pharmaceutical Research* 14 (1997), 969-975. Accordingly, this technique is not a fundamental solution to the problems caused by acidic elution buffer solutions.

A method has been proposed wherein a buffer solution replacement column is serially connected to the rear section of a column packed with protein A-binding support so that the buffer solution of antibody desorbed from protein A is replaced with neutral pH buffer solution within as short a time as possible. See Japanese Patent Application Publication No. Hei 1-135798. Although this method minimizes contact time, the change in antibody structure itself is not prevented. Thus, in the same manner as the above-cited method of JPA No. Hei 2-273194, this technique does not constitute a fundamental solution to the problems caused by acidic elution buffer solutions.

Based on the above-described prior art, the issues involved in solving the problems caused by acidic elution buffer solutions can be set forth as follows.

Utilizing the high affinity of protein A for antibody Fc domains requires the use of protein A as the ligand binding the antibody. An antibody desorption enhancer must be added to adequately lower the affinity of protein A to antibody Fc in a neutral pH buffer solution, or be of an acidity mild enough to prevent denaturation of the antibody by association or aggregation following binding of the antibody.

SUMMARY OF THE INVENTION

An object of the present invention is to provide a method of purifying an antibody comprising 1) conducting protein A affinity chromatography, and 2) desorbing said antibody by using an acidic buffer solution adjusted to pH 4.0 to 5.0 comprising arginine and/or a derivative thereof, and 3) recovering the antibody.

A further object of the present invention is to provide the method as stated above, wherein the concentration of said arginine and/or derivative thereof provides an antibody recovery rate equivalent to that of pH 3.5 sodium citrate buffer solution without inducing association or aggregation of the antibody.

DESCRIPTION OF THE PREFERRED EMBODIMENTS

To solve the problems of acidic elution buffer solutions in antibody purification, the present inventors extensively investigated antibody desorption enhancers. This resulted in the discovery that arginine, which is a natural amino acid, and/or an arginine derivative, effectively desorbed and recovered antibody bound to protein A at a mildly acidic pH. Arginine and/or arginine derivatives are known to effectively suppress the association and aggregation reactions of proteins. However, there have been no reports of any effect on the interaction of antibody and protein A. Arginine and/or arginine derivatives exhibit no denaturing action on proteins, are safe reagents for animals, including humans, and have ideal properties as reagents for recovering antibody in place of acidic elution buffer solutions.

Since the present invention permits the desorption and recovery of antibody from protein A-immobilizing support with a mildly acidic arginine and/or arginine derivative solution of pH 4.0 to 5.0, employing arginine and/or an arginine derivative as an elution enhancer has no effect on the affinity of protein A for antibody under neutral pH conditions, and consequently the high purification efficiency and impurity eliminating capability of protein A are fully preserved.

An easy method for removing the arginine and/or arginine derivative such as desalting or the like can be employed without destabilizing the tertiary structure of the antibody The antibody desorption enhancer employed in the present invention is the natural amino acid arginine and/or an arginine derivative obtained by chemically modifying arginine. Arginine derivatives include, in addition to arginine, acylated arginine such as acetyl arginine, agmatine obtained by removing a carboxyl group, and arginic acid obtained by incorporating a hydroxyl group in place of the α-amino group, and N-α-butyroyl-L-arginine and N-α-pyvaloyl arginine.

The solution containing arginine and/or an arginine derivative that is employed in the present invention may be a mildly acidic buffer solution of pH 4.0 to 5.0, preferably 4.3 to 4.7. Phosphate buffer solution or the like may be added.

The concentration of arginine and/or the arginine derivative is sufficient to exhibit an antibody recovery rate equivalent to that of pH 3.5 sodium citrate buffer solution without inducing association or aggregation of the antibody. For example, an arginine and/or arginine derivative concentration of from 0.1 to 4.0 M is suitable, 0.3 to 3.0 M is desirable, and 1 to 2 M is preferable.

Substances other than arginine and/or arginine derivatives may be contained in the buffer solution so long as they do not inhibit the purification of antibody by protein A affinity chromatography.

Commercially available protein A columns may be employed, for example, HiTrap r-Protein A FF (made by Amersham Bioscience, Inc.) may be used.

The antibody employed in the present invention may be any class or subclass of antibody for which protein A is known to be suitable, and may be similarly employed for any antibody-related protein with the Fc domains thereof binded. Furthermore, it may be employed irrespective of the purity of the purification starting materials. Examples include natural human antibodies, humanized and human-type antibodies prepared by genetic recombination, monoclonal antibodies of mice, and the like. Humanized and human-type monoclonal antibodies are the most useful from an industrial perspective, and are known to have relatively high affinity for protein A. Their elution from protein A columns requires buffer solutions of greater acidity as compared to monoclonal antibodies of mice, and the like. Accordingly, the present invention achieves its greatest effect with humanized antibodies and human-type antibodies.

In addition to the above, conditions that are conventionally employed in antibody purification employing protein A may also be employed in antibody elution methods employing arginine and/or an arginine derivative.

For example, mouse monoclonal antibody is dissolved in 20 mM glycine/NaOH buffer solution containing 3 M NaCl, or diluted tenfold with this buffer solution. This is then loaded onto a protein A column (for example, a HiTrap r-Protein AFF, made by Amersham Bioscience, Inc.) that has been equilibrated with the same buffer solution. The column is thoroughly washed with the same buffer solution to remove impurities derived from the starting materials, other than the antibody. A 0.1 to 3 M (desirably 0.3 to 3 M, preferably 1 to 2 M) arginine and/or arginine derivative elution buffer solution adjusted to from pH 4.0 to 5.0 (desirably from pH 4.3 to 4.7) is then run through the column and the desorbing antibody is recovered. When the recovered antibody is analyzed by gel permeation chromatography, it is found to elute out at the same retention time and in the same peak form as natural antibody, indicating that the antibody has undergone no tertiary structural change, association, or aggregation. When recovering antibody with acidic buffer solution of pH 4 or less (such as sodium citrate), it is well known that the recovered antibody tends to undergo association and aggregation when a certain concentration is reached.

In addition to the above-described monoclonal antibodies, the present invention may be similarly used to purify antibody in the form of natural human antibody, humanized antibody prepared by genetic recombination, or human-type antibody (these being collectively referred to herein as "human antibody") with arginine and/or an arginine derivative. An human antibody solution obtained by dissolving the antibody in a neutral pH buffer solution such as phosphate buffer solution, or diluting it about tenfold with such a solution, is loaded onto a protein A column (for example, a HiTrap r-Protein AFF, made by Amersham Bioscience Inc.) that has been equilibrated with the same buffer solution. Thorough washing is conducted with the same buffer solution to wash out starting material impurities, other than the antibody, after which, in the same manner as in the above-described mouse monoclonal antibody purification method, 0.1 to 3 M (desirably 0.3 to 3 M, preferably 1 to 2 M) arginine and/or arginine derivative solution that has been adjusted to from pH 4.0 to pH 5.0 is run through and the desorbing antibody is recovered. When the recovered antibody is analyzed by gel permeation chromatography, a peak of identical shape is found to elute out at the same retention time as for the natural state, and no change in the tertiary structure or association or aggregation is found to occur in the antibody. The lower limit at which the tertiary structure of the antibody can be retained is reported to be in the vicinity of pH 4.

Antibody solution that has been eluted out and recovered from an acidic citrate buffer solution is known to associate and aggregate within a short period, so immediate adjustment of the pH of the antibody to neutral following elution is advisable. However, in large-scale antibody manufacturing, rapid pH adjustment is difficult and sudden fluctuation in pH due to pH adjustment presents a substantial risk of antibody denaturation. In the desorption and recovery of antibody using the pH 4.0 to 5.0 arginine and/or arginine derivative solution of the present invention, the problems presented by acidic buffer solution are solved.

The present invention is specifically described below through embodiments; however, the present invention is not limited to these embodiments.

Example 1

A (3 mg) quantity of purified anti-vonWillebrand Factor monoclonal antibody (mouse antibody, subclass $IgG_1$; WO96/17078) is dissolved in isotonic sodium phosphate buffer solution to 5.28 mg/mL. 6.43 mL of 20 mM glycine/NaOH buffer solution (pH 8.9) containing 3 M NaCl was added to 0.57 mL of the antibody solution, to a total of 7 mL. This solution was loaded at a rate of 0.5 mL/min onto a 1 mL size HiTrap r-Protein AFF column (Amersham Biosciences, Inc.) that had been equilibrated with the same buffer solution, washed with 5 mL of the same buffer solution, and reequilibrated. The column was then loaded with 0.5 mL/min of the elution buffer solution shown in Table 1, and the desorbing and eluting antibody was recovered using ultraviolet absorption at a wavelength of 280 nm. The ultraviolet absorption of the obtained antibody solution was measured, the concentration of protein was calculated, whereby the degree of extinction coefficient exhibited by 1 mg/mL of the antibody solution was 1.4, and the amount of antibody recovered by this chromatography was determined. The entire operation was conducted at 5° C.

The results of elution and recovery of mouse monoclonal antibody with arginine or an arginine derivative are given in Table 1, and compared to elution and absorption conducted with 0.1 M sodium citrate at pH 3.5, which are widely employed as an acidic elution buffer solution for antibody. The recovery rate for each of the experiments is given as the ratio of the quantity of antibody in the recovered fraction to 3 mg of antibody loaded as starting material.

When 0.36 M or greater arginine (L-arginine, made by Ajinomoto) was employed, mouse monoclonal antibody was recovered under mildly acidic pH conditions of pH 4.30 or above with an efficiency just as good as when using a conventional acidic buffer solution.

Figure 1:
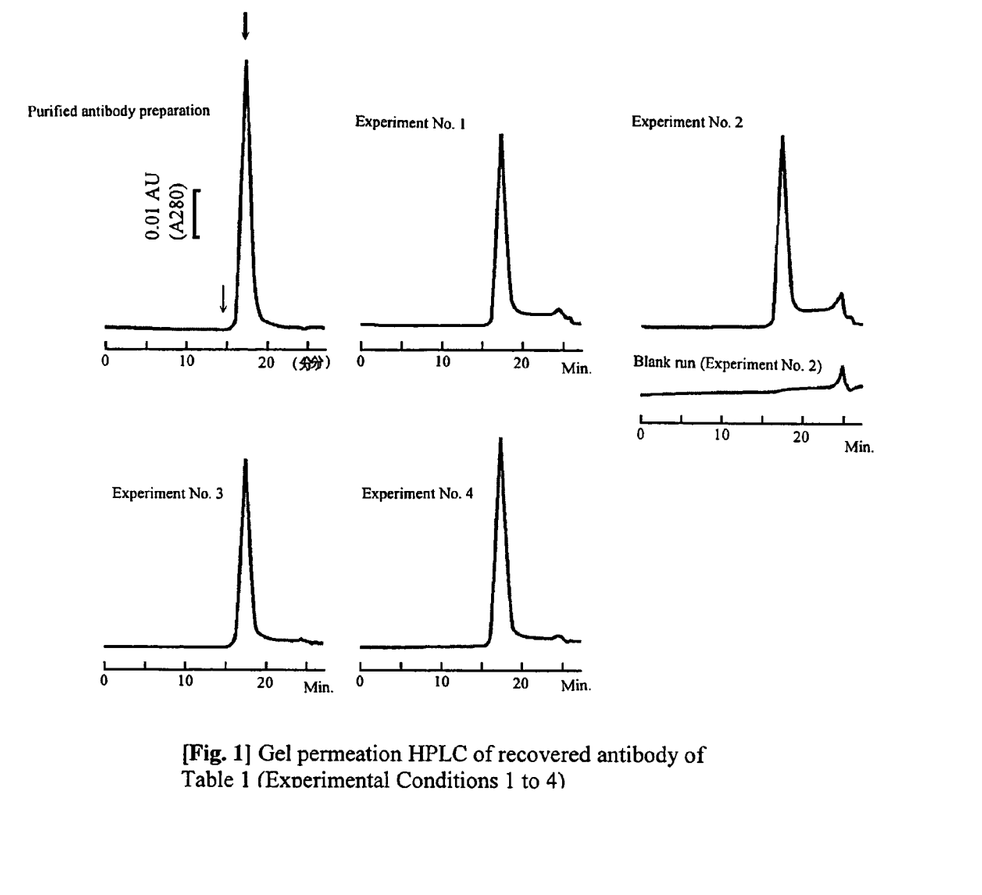
FIG. 1 shows gel permeation HPLC of the recovered antibody of Table 1.

FIG. 1 gives the results of analysis by gel permeation chromatography (column: Superdex 75HR 10/30, made by Amersham Bioscience, Inc., eluant: 0.2 M sodium phosphate, pH 4.0) for monoclonal antibody eluted and recovered with arginine (18 μg for Experiments 1 to 4). The X-axis denotes retention time (min). The results of analysis of just the elution buffer solution (a blank run) are given beneath Experimental Conditions 2. The peak at retention time 24 min. is due to the elution buffer solution.

Only a peak precisely matching that of natural antibody, indicated by the heavy arrow, was observed on the chromatogram of the purified antibody preparation. No association and aggregation (eluting at the location indicated by the thin arrow on the chromatogram of the purified antibody preparation) exceeding the lower limit of detection (1 percent) of the analysis method were found. Thus, structural change, association, and aggregation were found not to have occurred. In particular, the fact that mouse monoclonal antibody was recovered at pH 4.7 with 2 M arginine means that the problem of structural change accompanying contact with an acidic buffer solution was completely eliminated and the purification method was determined to be extremely effective. When antibody that was eluted and recovered with 0.1 M sodium citrate at pH 3.50 (Table 1, Experiment No. 11) was stored in a refrigerator, the solution gradually turned turbid and the quantity of antibody remaining in the supernatant decreased to ⅕ the level immediately following elution. By contrast, when antibody eluted and recovered with 1 M arginine at pH 4.30 (Table 1, Experiment No. 1) and 2 M arginine at pH 4.67 (Table 1, Experiment No. 2) were similarly stored in a refrigerator, no change such as turning turbid occurred and the quantity of antibody remained constant. This showed that in elution and recovery using arginine, the storage property of the antibody following elution and recovery was better than for conventional buffer solutions such as citric acid.

In the same manner as in the above-described elution of arginine, mouse monoclonal antibody was efficiently recovered at pH 4.35 with 0.36 M acetyl arginine (N-α-acetyl-L-arginine, made by Sigma Aldrich). Furthermore, mouse monoclonal antibody was also efficiently recovered at pH 4.32 with 1 M agmatine (made by Ajinomoto) in which the carboxyl group of arginine was removed. Analysis of the monoclonal antibody recovered with acetyl arginine and agmatine by the above-described gel permeation chromatography revealed only a peak precisely matching that of antibody in a natural state, with no association or aggregation exceeding the lower limit of detection (1 percent) of the analysis method being observed. Based on the above, as in the case of arginine, the elution and recovery of antibody with these arginine derivatives was found not to produce antibody structural change, association, or aggregation.

TABLE 1

Elution of mouse monoclonal antibody with arginine and arginine derivatives

| | Elution Conditions | | | Recovered Fractions | | | |
|---|---|---|---|---|---|---|---|
| Experiment No. | Buffer Solution | pH | Concentration (M) | Antibody Concentration (mg/mL) | Volume (mL) | Quantity of Antibody (mg) | Recovery Rate (%) |
| 1 | Arginine hydrochloride | 4.30 | 1 | 1.017 | 2.5 | 2.54 | 85 |
| 2 | | 4.67 | 2 | 0.932 | 2.5 | 2.33 | 78 |
| 3 | | 4.35 | 0.36 | 0.783 | 3.0 | 2.34 | 78 |
| 4 | | 4.03 | 0.36 | 0.898 | 2.6 | 2.33 | 78 |

TABLE 1-continued

Elution of mouse monoclonal antibody with arginine and arginine derivatives

| Experiment No. | Buffer Solution | pH | Concentration (M) | Antibody Concentration (mg/mL) | Volume (mL) | Quantity of Antibody (mg) | Recovery Rate (%) |
|---|---|---|---|---|---|---|---|
| 5 | Acetyl arginine hydrochloride | 4.35 | 0.36 | 0.955 | 2.5 | 2.39 | 80 |
| 6 |  | 4.12 | 0.36 | 1.009 | 2.5 | 2.52 | 84 |
| 7 |  | 4.04 | 0.36 | 1.029 | 2.5 | 2.57 | 86 |
| 8 |  | 3.83 | 0.36 | 0.966 | 2.5 | 2.41 | 80 |
| 9 |  | 3.54 | 0.48 | 0.974 | 2.5 | 2.44 | 81 |
| 10 | Agmatine phosphate | 4.32 | 1 | 0.276 | 8.5 | 2.35 | 78 |
| 11 | Sodium citrate | 3.50 | 0.1 | 0.921 | 2.5 | 2.30 | 77 |

Example 2

Cells derived from mouse myeloma were cultivated for one week in serum medium yielding 60 mL of culture supernatant, including impurities. This was loaded at 0.5 ml/min onto a HiTrap r-Protein AFF 1 mL column (Amersham Biosciences, Inc.) that had been equilibrated with isotonic phosphate buffer solution, yielding 60 mL of pass-through fraction. This fraction was handled as a model culture supernatant not containing any antibody produced by cells. 10.5 g of NaCl was added to 60 mL of the model culture supernatant and the mixture was lightly stirred and dissolved at 5° C. Next, the mixture was left standing for 30 min at 5° C. When the bubbles were found to have disappeared, 3 mg (3.28 mg/mL, 0.57 mL) of the same purified mouse monoclonal antibody as employed in Example 1 was added, and 1.2 mL of 1 M TrisHCl of pH 8.7 was added. The mixture was slowly stirred, after which the pH was adjusted to pH 8.9 with 0.5 M NaOH. The mixture was then loaded at 0.5 mL/min onto a HiTrap r-Protein AFF, 1 mL column (Amersham Biosciences, Inc.) that had been equilibrated with 10 mL of buffer solution (20 mM Gly/NaOH, 3 M NaCl, pH 8.9) and the column was washed with the same buffer solution until the baseline was restored. Subsequently, elution was conducted with the elution buffer solution shown in Table 2 and the same method as in Example 1 was employed to determine the recovery rate of the monoclonal antibody. The antibody concentration and recovery rate were calculated from the optical absorption of the recovered fractions. All operations were conducted at 5° C.

Figure 2:
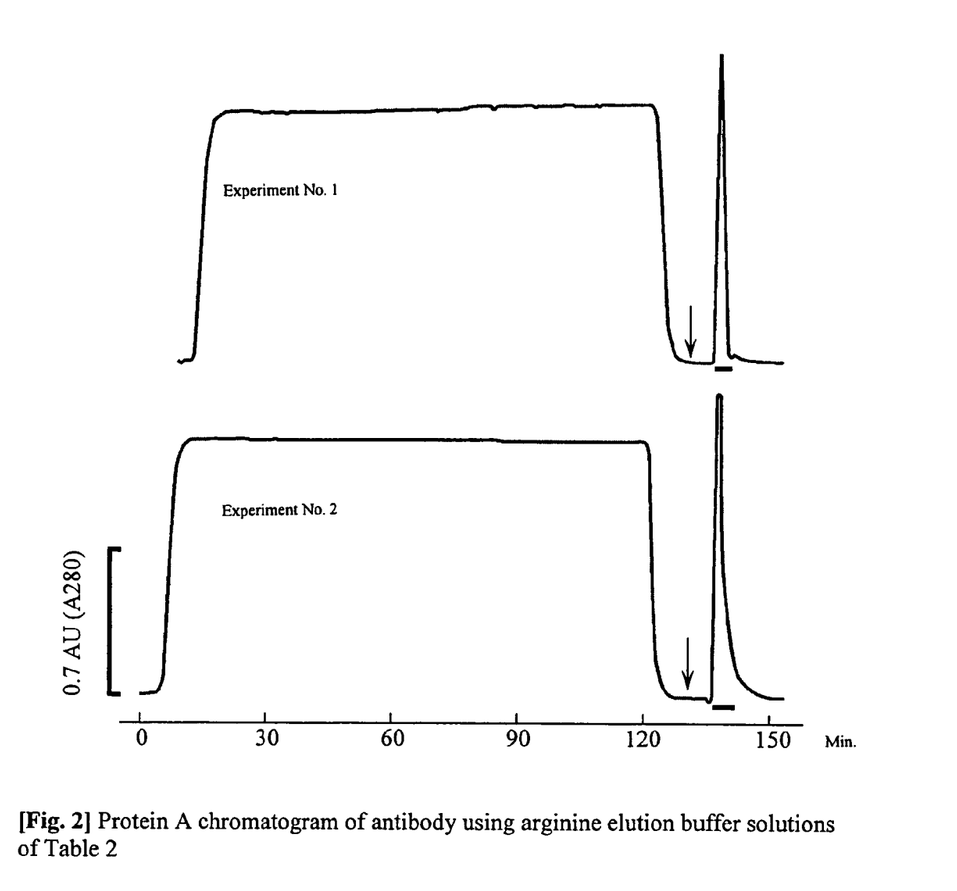
FIG. 2 shows protein A chromatogram of antibody using arginine elution buffer solutions of Table 2 (experiments 1 and 2).
Figure 3:
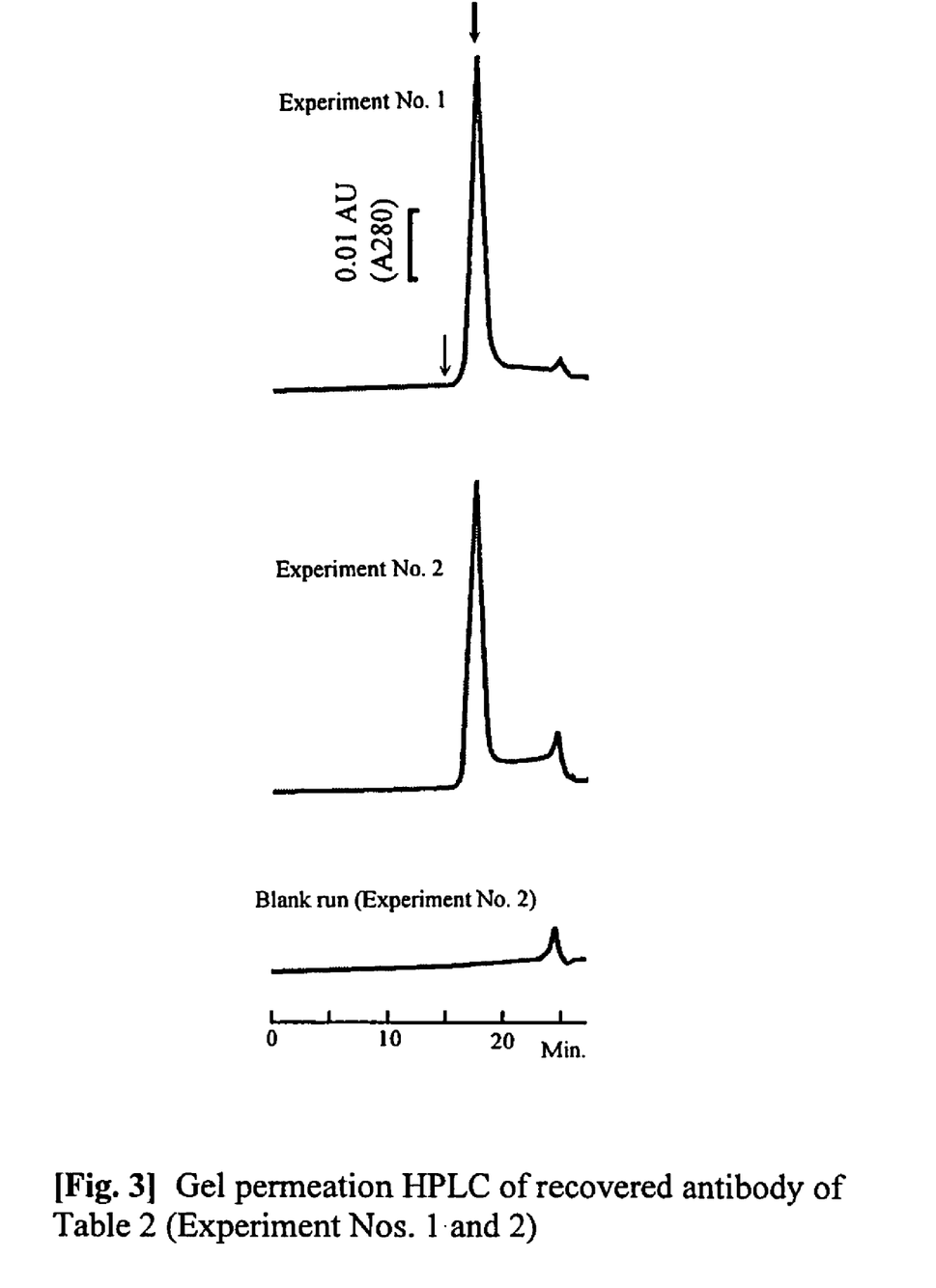
FIG. 3 shows gel permeation HPLC of recovered antibody of Table 2 (experiments 1 and 2).

Table 2 gives the recovery results, FIG. 2 shows the actual chromatograms, and FIG. 3 shows the results of analysis by gel permeation HPLC chromatography for the monoclonal antibody recovered (18 μg for Experiment 1 and 2 in table 2). In FIG. 2, antibody was eluted at the positions indicated by the arrows and under the conditions of Experiment 1 and 2 in table 2. The portions indicated by the horizontal bars beneath the peaks were subjected to recovery and analysis as antibody fractions. In FIG. 3, the x-axis denotes retention time (min.). It is shown from the blank run results, the peak around 24 min. was caused by the elution buffer solution.

The recovery rate of each experiment is given as the ratio of the quantity of antibody in the recovered fraction to the 3 mg of antibody loaded as starting material. Antibody solution containing impurity, even when loaded onto a protein A column, was efficiently recovered using a mildly acidic buffer solution containing arginine in the same manner as in Example 1. As indicated in FIG. 3, in both Experiment Nos. 1 and 2, the recovered antibody fractions exhibited only peaks precisely matching that of antibody in the natural state as indicated by the heavy arrow on the chromatogram of Experiment No. 1 (refer to FIG. 1 for the chromatogram of the refined antibody preparation). No association or aggregation (eluting out at the position indicated by the light arrow in the chromatogram of Experiment No. 1) exceeding the detection limit of the analysis method was observed. This completely eliminated the risk of structural change accompanying contact with an acidic buffer solution and indicated that the antibody purification method was extremely effective.

TABLE 2

Elution of mouse monoclonal antibody with arginine from starting material containing impurities

| Experiment No. | Buffer Solution | pH | Concentration (M) | Antibody Concentration (mg/mL) | Volume (mL) | Quantity of Antibody (mg) | Recovery Rate (%) |
|---|---|---|---|---|---|---|---|
| 1 | Arginine hydrochloride | 4.3 | 1 | 0.590 | 4 | 2.36 | 79 |
| 2 |  | 4.7 | 2 | 0.450 | 6 | 2.70 | 90 |

Example 3

Recombinant CHO cells (U.S. Pat. No. 5,854,070; ATCC Number CRL-11398) producing humanized antibody 6E6 to human CD 18 (integrin P2 subunit) were cultured for four days at 37° C. with a roller bottle in culture (αMEM) to which 10 percent fetal bovine serum (Invitrogen FBS, ultra-low IgG type) had been added, yielding a high cell density. Subsequently, the culture was transferred to fresh culture medium (ASF104, Ajinomoto) to which 2 percent fetal bovine serum (Invitrogen FBS, ultra-low IgG type) had been added, and culturing was continued for three days at 37° C., yielding culture supernatant containing antibody. 1 M Tris HCl of pH 8.5 to adjust the pH to 7.5 was added to 32 mL of this culture supernatant, after which the mixture was loaded at 0.4 mL/min onto an r-Protein AFF column (0.5 cm in diameter, 1 cm in length, 0.2 mL in size: Amersham Biosciences, Inc.) that had been equilibrated with isotonic phosphate buffer solution. The column was washed with the same buffer solution until the baseline UV absorption was restored, after which the elution buffer solutions shown in Table 3 were eluted. All of these operations were conducted at 5° C.

Figure 4:
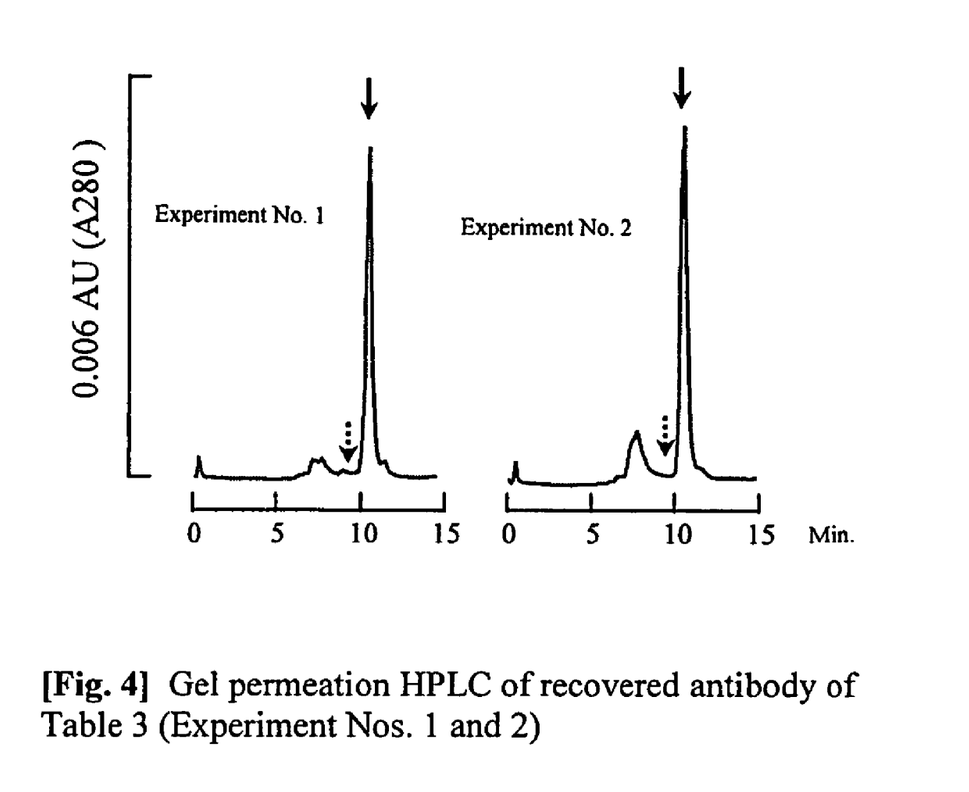
FIG. 4 shows gel permeation HPLC of recovered antibody of Table 3 (experiments 1 and 2).

Each 80 μL of recovered fraction was neutralized by the addition of 20 μL of 1 M Tris HCl of pH 8.5, of which 80 μL was used for gel permeation chromatography (column: TSK G3000SW$_{XL}$ made by Toso; eluant: 0.1 M sodium phosphate, pH 6.8). The results are given in Table 3 and FIG. 4. As shown in Table 3, the quantity of humanized antibody recovered with sodium citrate buffer solution and that recovered with arginine hydrochloric acidic buffer solution were nearly identical. Since the quantity of human antibody 6E6 contained in the culture supernatant starting material was unknown, the precise recovery rates in the present experiment could not be determined. However, it was clear that the two sets of elution conditions provided roughly the same capability. The antibody (about 2.5 μg) recovered in Experiments 1 and 2 of table 3 was analyzed by gel permeation HPLC under conditions shown above. The X-axis denotes retention time (min). As shown in FIG. 4, the purity of the antibody (the portion indicated by the solid arrow is antibody) in the fractions obtained under the two sets of elution conditions was nearly identical and the column retention times of the two peaks matched precisely. Further, the antibody association product is known to elute out at the position indicated by the dotted arrow. In the present example, in which the amount of antibody loaded onto the protein A column was small, neither the sodium citrate nor the arginine hydrochloride produced an association product exceeding 5 percent of the antibody. However, the sodium citrate (Experiment No. 1) was found to produce an antibody association product peak (dotted arrow), albeit slight. The above results indicated that humanized antibody was effectively eluted and recovered from protein A with a mildly acidic arginine buffer solution.

Example 4

Three arginine derivatives were prepared by the following method.

N-α-Butyroyl-L-Arginine: Arginine was dissolved in water/2-butanol, after which the reaction system was adjusted to pH 11 and 10-15° C. While maintaining the temperature and the pH with sodium hydroxide solution, butyroyl chloride was added dropwise and reacted. Following the reaction, purification was conducted with cation exchange resin, yielding a white solid. The structure and purity were determined by reverse phase HPLC and $^1$H-NMR.

N-α-Pyvaloyl-Arginine: Arginine was dissolved in water/2-propanol after which the system was adjusted to pH 11 and 10-15° C. While maintaining the temperature and the pH with sodium hydroxide solution, pyvaloyl chloride was added dropwise and reacted. Following the reaction, purification was conducted with cation exchange resin, yielding a white solid. The structure and purity were determined by reverse phase HPLC and $^1$H-NMR.

L-Arginic Acid: L-Arginine hydrochloride was dissolved in concentrated nitric acid/concentrated hydrochloric acid (1:2), then the system was heated to 60° C. and maintained for 30 minutes. The precipitating solid was recovered by filtration, dissolved in water, and hot refluxed until the starting material had completely disappeared. The reaction solution was concentrated and the precipitating solid was repeatedly recrystallized from water, yielding a white solid. The structure and purity were determined by reverse phase HPLC and $^1$H-NMR.

Recombinant CHO cells (U.S. Pat. No. 5,854,070; ATCC Number CRL-11398) producing humanized antibody 6E6 to human CD 18 (integrin β2 subunit) were cultured for four days at 37° C. with a roller bottle in culture medium (AMEM) to which 10 percent fetal bovine serum (Invitrogen FBS, ultra-low IgG type) had been added, yielding a high cell density. Subsequently, the culture was transferred to fresh culture medium (ASF104, Ajinomoto) to which 2 percent fetal bovine serum (Invitrogen FBS, ultra-low IgG type) had been added, and culturing was continued for three days at 37° C., yielding a culture supernatant containing antibody. 1 M Tris HCl of pH 8.5 to adjust the pH to 7.5 was added to 48 mL of the culture supernatant, after which the mixture was loaded at 0.4 mL/min onto an r-Protein AFF column (0.5 cm in diameter, 1 cm in length, 0.2 mL in size: Amersham Biosciences, Inc.) that had been equilibrated with isotonic phosphate buffer solution. The column was washed with the same buffer solution until the baseline UV absorption was restored,

TABLE 3

Elution of humanized antibody with buffer solutions of sodium citrate and arginine

| Experiment No. | Elution Conditions | | | Recovered Fractions | | Quantity of Antibody (μg) |
|---|---|---|---|---|---|---|
| | Buffer Solution | pH | Concentration (M) | Antibody Concentration (μg/mL) | Volume (mL) | |
| 1 | Sodium citrate | 2.9 | 0.1 | 30 | 0.45 | 14 |
| 2 | Arginine HCl | 4.3 | 1.0 | 29 | 0.40 | 12 | after which the flow was changed to 0.2 mL/min and the elution buffer solutions shown in Table 4 were eluted. All of these operations were conducted at 5° C. Each 80 μL of recovered fraction was neutralized by the addition of 20 μL of 1 M Tris HCl of pH 8.5, of which 80 μL was used for gel permeation chromatography (column: TSK G3000SW$_{XL}$ made by Toso; eluant: 0.1 M sodium phosphate, pH 6.8). The results obtained are given in Table 4 and FIG. 5.

TABLE 4

Elution of humanized antibody with arginine derivatives

| | Elution Conditions | | | Recovered Fractions | |
|---|---|---|---|---|---|
| Experiment No. | Buffer Solution | pH | Concentration (M) | Antibody Concentration (μg/mL) | Volume (mL) | Quantity of Antibody (μg) |
| 1 | N-α-Butyroyl-L-arginine | 4.3 | 0.92 | 35 | 0.85 | 30 |
| 2 | N-α-Pyvaloyl-arginine | 4.3 | 0.85 | 36 | 0.70 | 25 |
| 3 | Arginic acid | 4.3 | 1.00 | 36 | 0.70 | 25 |

Figure 5:
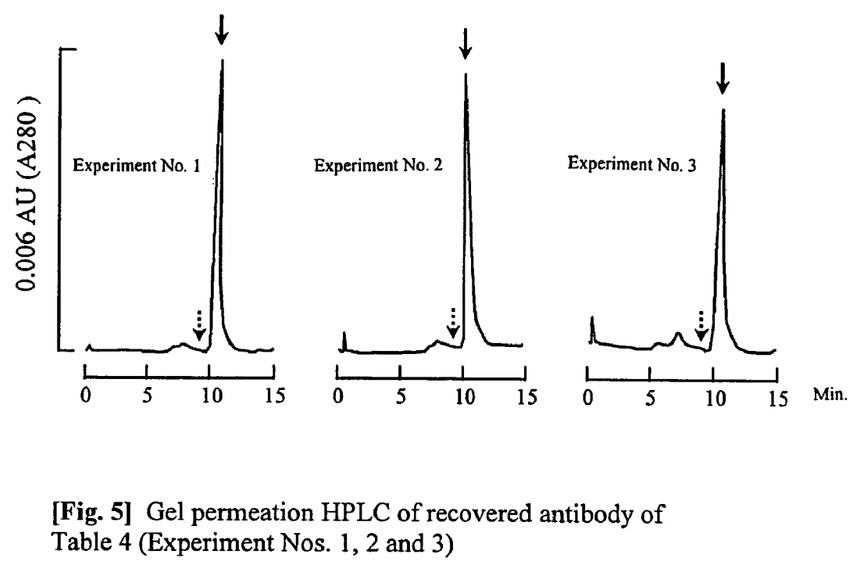
FIG. 5 shows gel permeation HPLC of recovered antibody of Table 4 (experiments 1, 2 and 3).

As indicated in Table 4, the quantities of humanized antibody recovered with the three arginine derivatives were nearly identical. This clearly indicated that the arginine derivatives had nearly the same elution capability. The antibody (about 2.5 μg) recovered in Experiments 1, 2, and 3 of table 4 was analyzed by gel permeation HPLC under conditions given above. The x-axis denotes time (min.). As shown in FIG. 5, the antibody purity in the fractions obtained (the portion indicated by the solid arrow is antibody) was nearly identical for the three arginine derivatives and the retention times of the respective antibody peaks perfectly matched the elution peak of sodium citrate in Example 3. Antibody association product is known to elute at the position indicated by the dotted arrow. In none of these three cases did the amount of antibody association product generated exceed 5 percent of the antibody. These results indicated that humanized antibody could be effectively eluted and recovered from protein A with mildly acidic arginine derivatives.

Figure 6:
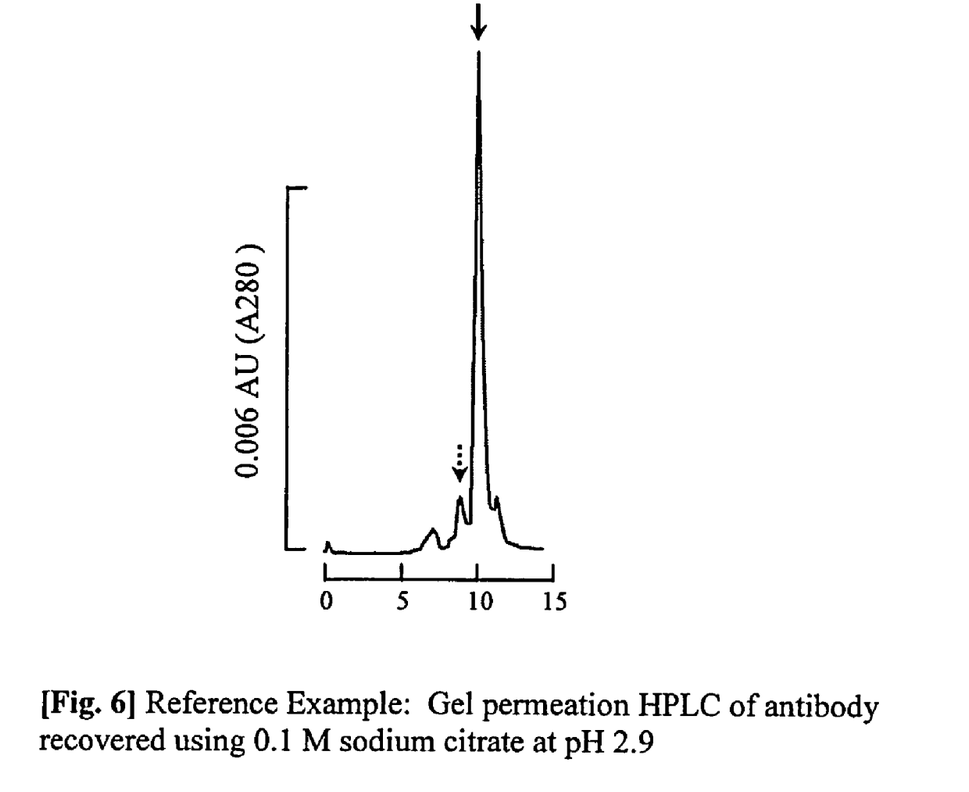
FIG. 6 shows the Reference Example: Gel permeation HPLC of antibody recovered using 0.1 M sodium citrate at pH 2.9

As a reference example, 1,000 mL of the same culture supernatant as employed in Examples 3 and 4 was loaded onto a HiTrap r-Protein AFF 1 mL column (Amersham Biosciences, Inc.), thorough washing was conducted with isotonic phosphate buffer solution, and elution was conducted with the same 0.1 M sodium citrate as in Experiment No. 1 of Table 3 at pH 2.9. The quantity of antibody loaded onto the column was more than 20 times that employed under the conditions of Examples 3 and 4. The antibody fraction obtained was subjected to gel permeation HPLC following neutralization titration in the same manner as in Example 3; the results are given in FIG. 6. The solid arrow indicates antibody and the dotted arrow indicates antibody association product. Antibody association product was found to have been produced by the acidic buffer solution (sodium citrate).

While the invention has been described with reference to preferred embodiments thereof, it will be apparent to one skilled in the art that various changes can be made, and equivalents employed, without departing from the scope of the invention. Each of the aforementioned documents is incorporated by reference herein in its entirety.

We claim:

1. A method of purifying an antibody comprising
   a) placing a starting material containing said antibody on a protein A affinity chromatography column,
   b) desorbing said antibody from said column using a buffer solution adjusted to pH 4.0 to 5.0 comprising arginine and/or a derivative thereof, and
   c) recovering the antibody, wherein the concentration of said arginine and/or derivative thereof provides an antibody recovery rate equivalent to that of pH 3.5 sodium citrate buffer solution.

2. The method of claim 1, wherein said antibody recovery does not induce association or aggregation of the antibody.

3. The method of claim 1, wherein said starting material is selected from the group consisting of a monoclonal antibody solution, a mouse myeloma cell solution, a humanized antibody-producing cell solution and a human-type antibody-producing cell solution.

4. The method of claim 1, wherein said starting material is humanized antibody-producing cells, human-type antibody-producing cells, a humanized antibody-producing cell solution and a human-type antibody-producing cell solution.

5. The method of claim 1, wherein said starting material is CHO cells.

6. The method of claim 1, wherein said buffer solution is adjusted to pH 4.3 to 4.7.

7. The method of claim 1, wherein the concentration of said arginine and or arginine derivative is from 0.1 to 4.0 M.

8. The method of claim 7, wherein the concentration of said arginine and or arginine derivative is from 1 to 2 M.

9. The method of claim 1, wherein said antibody is selected from the group consisting of a natural human antibody, a humanized antibody, a human-type antibody, an antibody prepared by genetic recombination and a monoclonal antibody.

10. The method of claim 1, wherein said antibody is selected from the group consisting of a natural human antibody, a humanized antibody and a human-type antibody.

11. A method of purifying an antibody comprising
    a) placing a starting material containing said antibody on a protein A affinity chromatography column,
    b) desorbing said antibody from said column using a buffer solution adjusted to pH 4.0 to 5.0 comprising arginine and/or an arginine derivative, and
    c) recovering the antibody,
wherein said arginine derivative is selected from the group consisting of acetyl arginine, agmatine, L-arginic acid, N-α-butyroyl-L-arginine, and N-α-pyvaloyl arginine.

12. The method of claim 11, wherein said arginine derivative is N-α-butyroyl-L-arginine.

13. A method of producing a purified antibody comprising:
   a) placing a starting material containing an antibody on a protein A affinity chromotography column,
   b) desorbing said antibody from said column using a buffer solution adjusted to pH 4.0 to 5.0 comprising arginine and/or an arginine derivative, and
   c) recovering the antibody, wherein said arginine derivative is selected from the group consisting of acetyl arginine, agmatine, L-arginic acid, N-α-butyroyl-L-arginine, and N-α-pyvaloyl arginine, wherein the concentration of said arginine and/or derivative thereof provides an antibody recovery rate equivalent to that of pH 3.5 sodium citrate buffer solution.

14. The method of claim 11, wherein said arginine derivative is N-α-butyroyl-L-arginine.

* * * * *